United States Patent [19]

King

[11] Patent Number: 4,754,753

[45] Date of Patent: Jul. 5, 1988

[54] SYSTEM FOR SENSING ELECTRICAL DEPOLARIZATION WAVE SIGNALS AND THEIR DIRECTION

[75] Inventor: Wendell L. King, North Oaks, Minn.

[73] Assignee: Medtronic, Inc., Minneapolis, Minn.

[21] Appl. No.: 797,359

[22] Filed: Nov. 12, 1985

Related U.S. Application Data

[63] Continuation of Ser. No. 262,863, May 12, 1981, abandoned.

[51] Int. Cl.$^4$ .............................................. A61B 5/04
[52] U.S. Cl. .............................. 128/699; 128/419 D; 128/786
[58] Field of Search .............. 128/419 D, 419 P, 642, 128/644, 699, 705, 784–786

[56] References Cited

U.S. PATENT DOCUMENTS

| | | | |
|---|---|---|---|
| 3,548,813 | 12/1970 | Berner | 128/419 P |
| 3,710,174 | 1/1973 | Cerniglia, Jr. | 315/22 |
| 3,815,611 | 6/1974 | Denniston | 128/419 D |
| 3,825,015 | 7/1974 | Berkovits | 128/419 P |
| 3,915,174 | 10/1975 | Preston | 128/419 P |
| 3,937,226 | 2/1976 | Funke | 128/419 D |
| 3,942,536 | 3/1976 | Mirowski et al. | 128/419 D |
| 3,983,867 | 10/1976 | Case | 128/2.06 G |
| 4,121,575 | 10/1978 | Mills et al. | 128/734 |
| 4,172,451 | 10/1979 | Kline | 128/642 |
| 4,216,780 | 8/1980 | Rubel et al. | 128/699 |
| 4,224,949 | 9/1980 | Scott et al. | 128/734 |
| 4,354,497 | 10/1982 | Kahn | 128/419 D |
| 4,365,639 | 12/1982 | Goldreyer | 128/786 |

FOREIGN PATENT DOCUMENTS 670299  6/1979  U.S.S.R. .......................... 128/419 D

OTHER PUBLICATIONS

Article entitled "Engineering Aspects of Implantable Cardiac Pacemakers", by P. Tarjan, published in Cardiac Pacing, P. Samet Editor, New York, 1973, pp. 47–71.

Article entitled "A Comparison of Unipolar and Bipolar Electrograms for Cardiac Pacemaker Sensing", by DeCaprio et al., published in Circulation, vol. 56, No. 5, Nov. 1977, pp. 750–755.

Abstract entitled "Proposed Cardiac Pacemaker System Combining Unipolar Stimulation with Bipolar Sensing", by Hurzeler et al., published in IEEE Transactions on Biomedical Engineering, vol. BME-26, No. 7, Jul. 1979, p. 440.

Article entitled "Conduction Cardiograph-Bundle of His Detector", published in IEEE Transactions on Biomedical Engineering, vol. BME-22, pp. 269–274, Jul. 1975.

*Primary Examiner*—Max Hindenburg
*Attorney, Agent, or Firm*—Reed A. Duthler; Joseph F. Breimayer; John L. Rooney

[57] ABSTRACT

Apparatus and method for sensing the probable onset of ventricular fibrillation or other harmful tachyarrhythmias and delivering electrical cardioverting stimulation pulses in response thereto. The sensing of the onset of the harmful tachyarrhythmia is accomplished using two different types of sensors. The first sensing technique utilizes an intracardiac ECG observed within three dimensional space. Directional changes of the current vector within the intracardiac ECG are used to predict the onset of harmful ventricular tachyarrhythmias. The second sensing technique employs a chemically sensitive semiconductor device which measures the level of ionic potassium found within the intracardiac blood. Rapid changes in ionic potassium level are used to predict the onset of detrimental ventricular tachyarrhythmias. An implantable device uses both types of sensors in a programmable fashion to deliver cardioverting electrical stimulation pulses based upon the predicted onset of ventricular fibrillation.

15 Claims, 9 Drawing Sheets

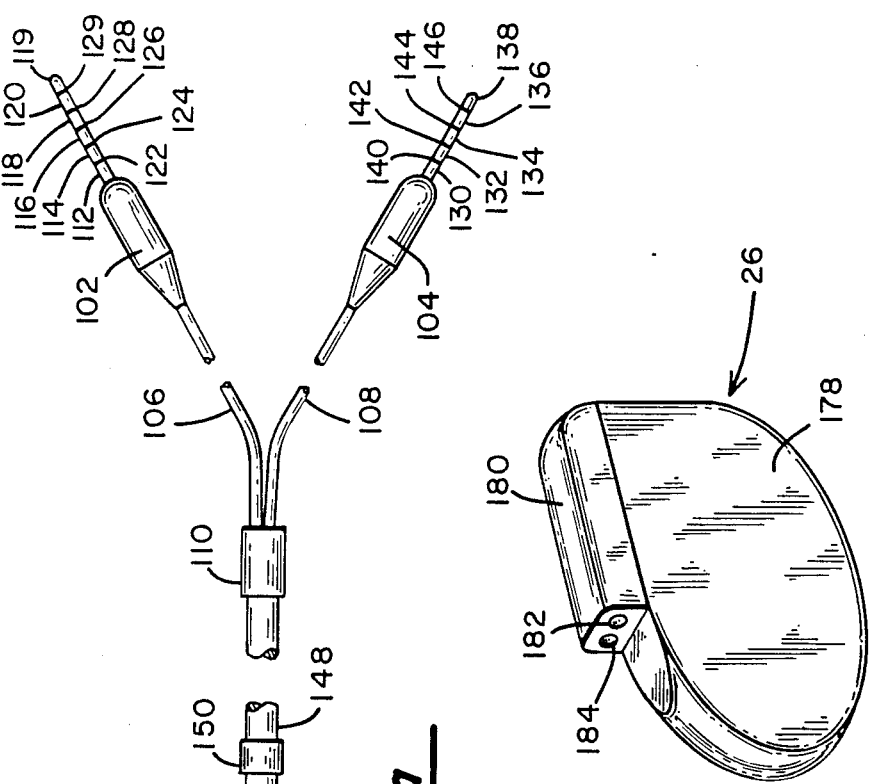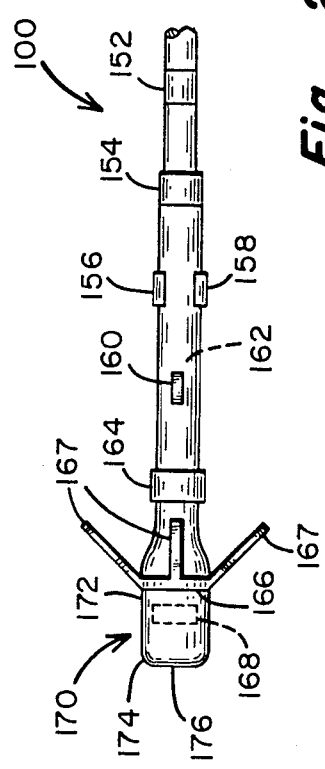

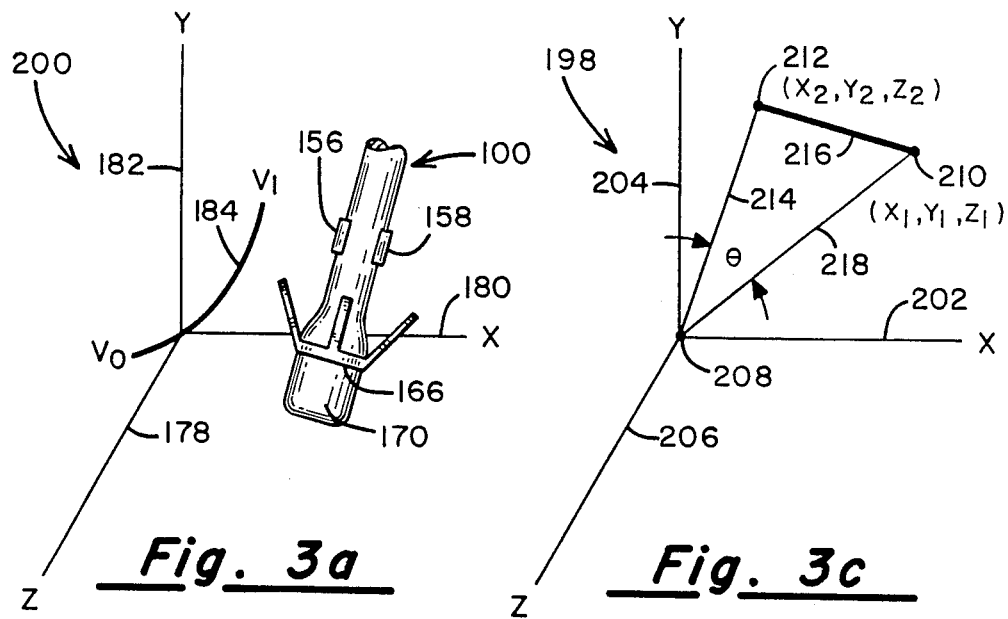
Fig. 3a
Fig. 3c
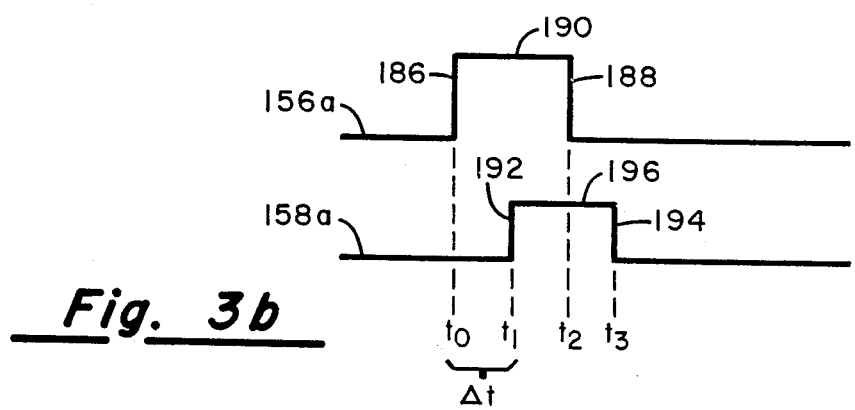
Fig. 3b
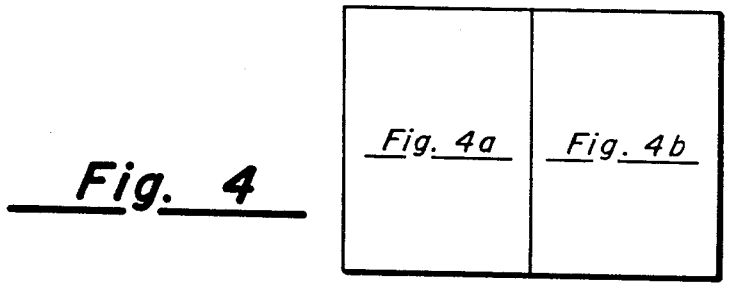
Fig. 4
Fig. 4a | Fig. 4b

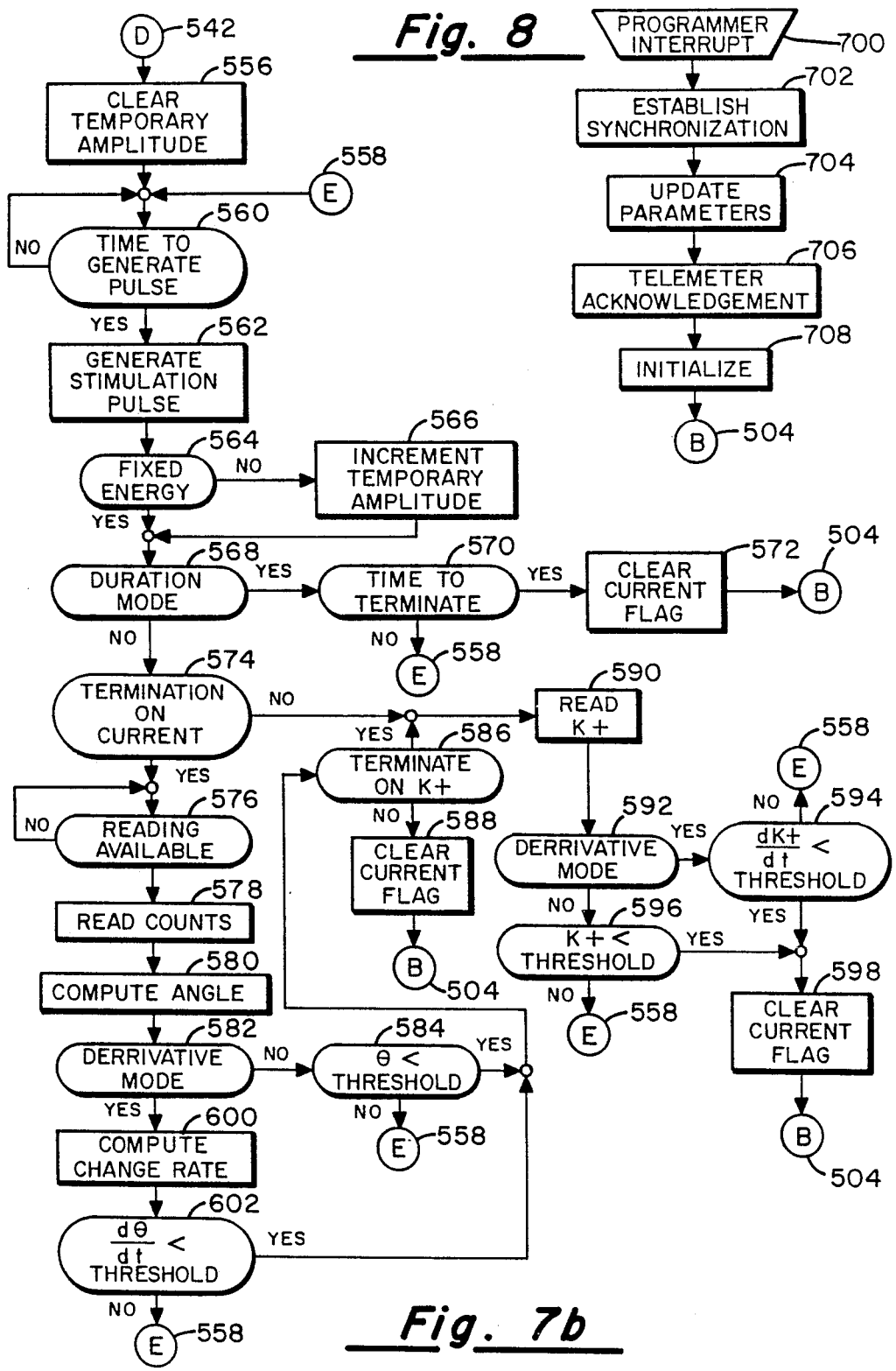

SYSTEM FOR SENSING ELECTRICAL DEPOLARIZATION WAVE SIGNALS AND THEIR DIRECTION

This is a continuation of co-pending applicaiton Ser. No. 262,863 filed on May 12, 1981, abandoned Aug. 14, 1987.

BACKGROUND OF THE INVENTION

1. Field of the Invention

The present invention relates generally to medical electronic devices and, more particularly, relates to implantable devices useful for the correction of cardiac arrhythmias.

2. Description of the Prior Art

The problem of sudden patient deaths from ventricular tachyarrhythmias and particularly fibrillation has been addressed for some time. Nearly every intensive care unit and cardiac care unit within a major hospital has defibrillation equipment readily available. A characteristic of this equipment is that it is used externally and must be operated by trained medical personnel. A safe and effective implantable automatic defibrillator has been envisioned for some time. Such a device would be implanted in a patient having a high probability of sudden death from ventricular fibrillation and would operate automatically to cardiovert a patient's heart regardless of the patient's location of instant activity.

Mirowski et al, in U.S. Pat. No. 3,614,955, disclose an early implantable defibrillator employing therefor an implantable pressure transducer to detect fibrillation. Specifically, whenever a pressure transducer located within the right ventricle ceases to record the normal pressure transitions attendant to pumping activity, a defibrillation pulse is generated and applied to the tissue. This approach has two basic difficulties. Although a great deal of work has been undertaken in the nearly ten years since the issue of the patent, effective chronically implantable pressure transducers are difficult to fabricate and are expensive to produce. The second problem with the device taught by Mirowski et al relates to the fact that the apparatus does not attempt to apply a cardioverting signal until such time as the patient's heart has actually entered into ventricular fibrillation.

A later and more sophisticated implantable defibrillator is taught by Rizk in U.S. Pat No. 4,114,628. This device senses both the mechanical activity of the patient's heart and the electrical activity. As has become known, merely sensing electrical activity in terms of a normal ECG is insufficient to detect the onset of fibrillation because, in many patients, the right ventricle may appear to have a normal ECG signal but, in effect, not be pumping an adequate supply of blood. Therefore, Rizk utilizes a comparision circuit for comparing the mechanical activity with the electrical activity of heart. Such a comparison is used to determine whether or not the patient's heart is indeed properly responding to the electrical stimulus present. As with the approach of Mirowski, et al., this technique essentially awaits right ventricular fibrillation before a stimulation pulse is applied. As has been proven many times in actual experimentation, the greater the delay in applying the defibrillator pulse after the onset of ventricular fibrillation, the larger the energy required in the pulse to accomplish defibrillation. In addition, it is reasonable to expect that the longer defibrillation is delayed, the greater the trauma inflicted upon the patient.

Furthermore, the size and cost of the implantable device is directly related to the amount of energy required to effect defibrillation, and it is desirable to reduce the energy required to both reduce patient trauma and to decrease the size and cost of the implantable device.

Electrodes for successful defibrillation after some delay may be seen in U.S. Pat. No. 4,030,509 issued to Heilman et al. As can be seen, these electrodes are prepared to handle relatively large energy stimulation pulses. Again, such large energy pulses are required if substantial delay is encountered between the onset of the initial ventricular tachycardia and the application of the cardioverting pulse.

A more recent implantable defibrillator is disclosed in U.S. Pat. No. 4,184,493 issued to Langer et al. This reference teaches detection of the onset of ventricular fibrillation by sophisticated processing of an intracardiac ECG signal. As discussed above, this technique may be very effective in many cases, however, it is known that for some period of time ventricular fibrillation may occur before it is detectable within the ECG signal. The effect of this delay is again the requirement that a larger energy is used for the defibrillating stimulation pulse.

One can see from these references and other available in the field deemed no more pertinent than these cited that the difficulty associated with the implantable defibrillator involves the use of the proper sensor or sensor combination offering a high reliability prediction of the onset of fibrillation. This prediction offers low energy and low patient trauma cardioversion. Indeed, the ultimate goal is prevention of ventricular fibrillation by early intervention.

SUMMARY OF THE INVENTION

The present invention incorporates two types of sensors to indicate the onset of fibrillation. Because these techniques have been shown experimentally to predict fibrillation before the actual occurrence, the stimulation pulse produced by the programmable apparatus in response thereto, is of relatively low energy. The lower limit of the stimulation energy required is that of a normal pacing pulse.

The first of the two sensors measures the current vector in three dimensional space within the myocardium. Ventricular fibrillation is predicted in part based upon relatively large changes in the direction of this current vector. Notice that this is substantially different from predicting the onset of fibrillation from changes in the amplitude which are normally sensed much later in the ventricular tachyarrhythmia process. Experimental evidence has shown that ventricular fibrillation can be predicted as the result of large changes in direction of this current vector.

The second sensor employed is a chemical sensor which measures the content of extracellular potassium ions within the blood. Other experimental data has shown that the onset of ventricular fibrillation may almost always be predicted by imbalance of this critical ion. In fact, many researchers believe that the improper amount of extracellular ionic potassium may, in fact, be one cause of ventricular fibrillation.

The current vector and extracellular potassium ion level information is used to predict the onset of ventricular fibrillation using thresholds which are readily programmable by the attending physician using external equipment. One or the other or both sensors may be used for triggering of a stimulation pulse. This stimulation pulse is also programmable in frequency and energy output.

It is believed that the present invention measures those parameters most associated with early prediction of the onset of ventricular fibrillation. Therefore, relatively low energy levels are used to reestablish proper ventricular rhythm. Because low energies are used, small device size and cost are readily available.

BRIEF DESCRIPTION OF THE DRAWINGS

FIG. 2a is a plan view of a transvenous lead containing both sensors and stimulation electrodes for practicing the present invention.

FIG. 2b is a view of the distal end of the transvenous lead of FIG. 2a.

FIG. 2c is a plan view of an implantable pulse generator for use with the present invention.

FIG. 3a is diagrammatic view of the way in which a single electrode pair of the implantable transvenous lead of FIG. 2a measures the direction of a current vector in three dimensional space.

FIG. 3b is a timing diagram showing the waveforms sensed by the electrode pair of FIG. 3a after processing.

FIG. 3c shows the derivation of the angular change of direction of the sensed current vector of the intracardiac ECG within three dimensional space.

FIG. 8 is a flowchart of the firmware routine for handling interrupts to microprocessor 336.

DETAILED DESCRIPTION OF THE PREFERRED EMBODIMENT

The following description discloses the inventor's preferred manner of employing the present invention. This preferred mode utilizes an implantable transvenous intracardiac lead, an implantable pulse generator, and an external programmer. Using these three major elements in the manner taught herein, one can produce a practical device for the automatic prevention of ventricular fibrillation. Those of ordinary skill in the art, however, will be able to readily apply the present invention as herein disclosed to other types of systems for the treatment of other types of arrhythmias and other physiological conditions.

Figure 1:
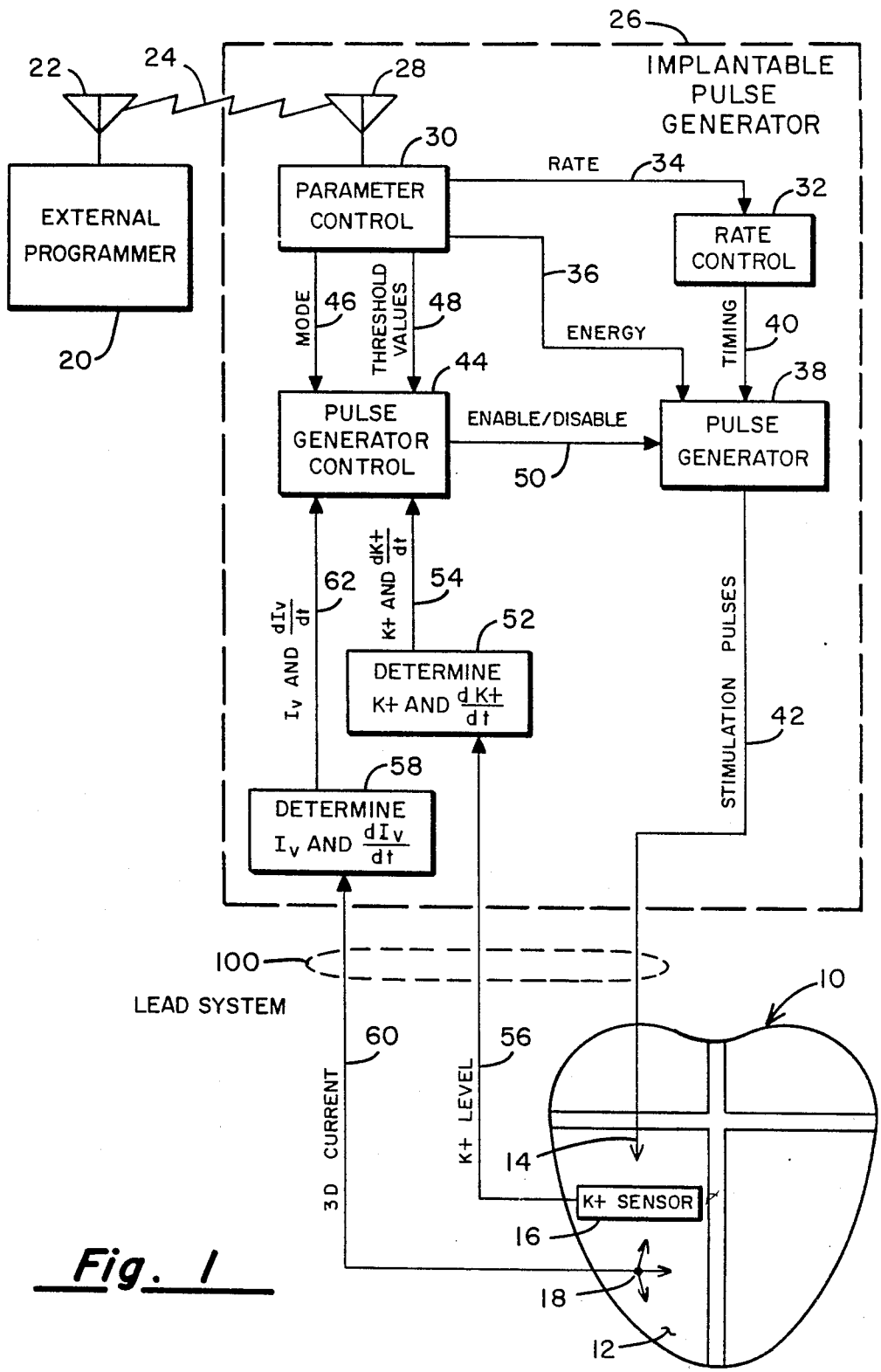
FIG. 1 is a functional block diagram of the major operating elements of an implantable automatic fibrillation prevention device.

FIG. 1 is an overall pictorial diagram of an automatic implantable fibrillation prevention system. This diagram depicts the operation of the preferred mode of the present invention in the functional manner and does not necessarily depict the way that the various hardware and software elements are partitioned. Nonetheless, it is felt to be an important and necessary way of depicting the operation of the preferred mode for greatest understanding of its operation.

External programmer 20 is a device common in the art of implantable programmable devices which allow parameter entries to be made to the implantable device. It is normally operated by the attending physician or other highly trained medical person and is not intended to be used by the patient. External programmer 20 communicates with implantable pulse generator 26 via RF signal 24 transmitted by RF antenna 22. Those interested in the detailed operation of a programmer, e.g. 20, may consult U.S. Pat. No. 4,236,524 issued to Powell et al. assigned to the assignee of the present invention. This patent teaches a state of the art programmer currently in use by the assignee of the present invention. Furthermore, this programmer and the techniques and features used therein are considered to be the best mode of practising the present invention.

Parameter control 30 receives RF signal 24 via RF antenna 28. Parameter control 30 is located, of course, within implantable pulse generator 26 as shown. It receives two types of data are associated with the sensing control and two types of data are associated with control of the stimulation pulse.

Mode information is sent from parameter control 30 to pulse generator control 44 via line 46 as shown. This mode information determines what sensed information is to be assumed to constitute the indication of onset of ventricular fibrillation. The mode information may thus describe whether current vector data, ionic potassium (K+) data or both are required to initiate stimulation. Once initiated, the mode data also determines the type of stimulation to be supplied.

The second type of data that influences the sensing process are the threshold values which are transferred from parameter control 30 to pulse generator control 44 via line 48. The threshold values describe what specific changes in current vector direction and potassium ion concentration are to be considered normal and which are to be considered abnormal. The specific values of these parameters are discussed in detail below.

The two types of data to be used in controlling the stimulation pulse are rate, which is transferred from parameter control 30 to rate control 32 via line 34 and energy level which is transferred via line 36 from parameter control 30 to pulse generator 38. As with those parameters affecting the sensing process, these parameters are discussed in detail below.

Lead system 100 consists of three lead conductor groups illustrated in FIG. 1 as llines 42, 56 and 60. Line 60 transfers the three directional current as sensed by electrode 18 to "determine $I_V$ and $dI_V/dt$" block 58. Similarly, K+ sensor 16 transfers its output via line 56 to "determine K+ and $dK+/dt$" block 52. Line 42 conducts the stimulation pulse from pulse generator 38 to the right ventricular tissue to be stimulated (i.e., near right ventricular apex). Although these may represent multiple lead configurations, the preferred mode is to incorporate all of these lines into a single lead system 100 wherein the distal ends of each of lines 42, 56, and 60 lie within the right ventricle 12 of the heart 10. It is preferable that lead system 100 be a transvenous lead.

Line 60 conducts the 3D current signal from sensing electrodes in the heart to the "determine $I_V$ and $dI_V/dt$" block 58 in the implantable pulse generator 26. The current vector and the time rate of change of current vector are determined in block 58 and forwarded to pulse generator control 44 via line 62. This determination is made in a digital fashion and involves resolving certain electrical signals within an arbitrary three dimensional coordinate system. The signal $I_V$ is an angle $\theta$ measured from an arbitrary vector and $dI_V/dt$ is the change in $\theta$ relative to time. Pulse generator control 44 uses this information as part of its input to determine when the stimulation pulses should be supplied and when stimulation should be terminated.

Potassium ion sensor 16 is an ionic selective field effect transistor which measures the amount of extracellular potassium ions within the intracardiac blood. This value is supplied via line 56 to "determine K+ and dK+/dt" block 52 for a determination of the ionic potassium level in millimoles per liter and for determination of the time rate of change of ionic potassium level. The resultant signals are supplied via line 54 to pulse generator control 44.

Pulse generator control 44 uses the mode data received via line 46, the threshold values supplied by line 48, the current vector and derivative of current vector data supplied via line 62, and the K+ and derivative of K+ value supplied by line 54 to determine when pulse generator 38 should be enabled and disabled. The actual control signal generated by the pulse generator control 44 is supplied by line 50. The determination is a purely binary one and is based upon arithmetic computations. Pulse generator control 44 implements certain of its functions within an implantable microprocessor structure.

Pulse generator 38 supplies a stimulation pulse via line 42 to the right ventricular endocardial tissue of heart 10. Timing for the stimulation pulses is supplied by rate control 32 via line 40 as shown. It is contemplated that the pulse generator stimulation pulse rate and energy are programmed via external programmer 20 and are received from rate control 32 and parameter control 30 via lines 40 and 36. As stated above, line 50 simply enables or disables the stimulation pulses.

As can be seen from a detailed examination of FIG. 1, many of the functions (i.e., external programmer 20, parameter control 30, rate control 32, and pulse generator 38) are similar to functions commonly implemented in the state-of-the-art implantable cardiac pacemaker pulse generators (e.g., those found in commonly assigned U.S. Pat. No. 4,236,522 issued to McDonald et al). Therefore, little additional detailed description is given of these functions. The text below concentrates more upon lead system 100 and the other aspects of implantable pulse generator 26 which are, of necessity, new and novel within the present invention.

FIG. 2a is a plan view of an endocardial lead incorporating all of the electrodes and sensors required for practicing the present invention in the preferred mode. As stated above, it is preferable that the lead system herein denoted by reference numeral 100 be of the transvenous variety which permits minimal trauma to be induced in the patient during the implant procedure. At the distal tip of lead system 100 is protective dome 170 which serves two basic functions. It serves as the stimulation cathode and accordingly, must be made of a body implantable conducting material (e.g. Titanium) Secondly, protective dome 170 protects and shields the K+ sensor 168 shown in the dashed lines. The presence of protective dome 170 protects the delicate component parts of K+ sensor 168 while allowing access of intracardiac blood to K+ sensor 168 through distal opening 176. Should it be desirable to decrease the effective stimulation surface area of protective dome 170, part of its surface may be covered with a nonconducting substance such as parylene coating 172 leaving only stimulation surface 174.

FIG. 2b is a view of lead system 100 as seen from the distal end. Protective dome 170 has a large circular opening 176 (see also FIG. 2a) to permit intracardiac blood to impinge upon K+ Sensor 168.

Acute and chronic fixation of the transvenous lead assembly is achieved via tine assembly 166 with tines 167 attached thereto. Such manner of fixation is described in commonly assigned U.S. Pat. No. 3,902,501 issued to Citron et al.

Referring again to FIG. 2a electrodes 164 and 154 are ring electrodes which go around the entire circumference of the lead body. Sensing electrodes 160, 162 (obscured by the lead body) 156 and 158 on the other hand are partial plate electrodes which do not conduct around the entire circumference of the lead. Electrodes 164, 160, 162, 156, 158 and 154 are six electrodes which comprise the three dimensional current sensing system. Structurally, each is connected through a different conductor within the lead body to a different connection surface at the proximal end of the lead. Such electrical isolation is necessary to enable resolving the current vectors in three dimensional space. The manner of processing the signals to accomplish this is discussed in detail below.

Electrodes 160 and 162 are located opposite one another on the lead body. Similarly, electrodes 156 and 158 are displaced 180° from one another and displaced 90° from sensing electrodes 160 and 162. As can be seen, therefore, sensing electrodes 164 and 154 comprise an electrode pair to sense currents in the direction of the longitudinal axis of lead system 100. Sensing electrodes 160 and 162 comprise an electrode pair for sensing currents in the direction perpendicular to the plane of FIG. 2a. Similarly, sensing electrodes 156 and 158 comprise an electrode pair suitable for sensing currents within the plane of FIG. 2a and perpendicular to the main axis of lead system 100. Should the reader desire additional structural details of the construction of the three electrode pairs, he may consult commonly assigned U.S. patent application Ser. No. 230,572 filed Feb. 2, 1981. Electrical operation of the six sensing electrodes is discussed in detail below.

Reference electrode #2 152 is located as shown. As is discussed below in detail, the gate current path for the K+ ion sensitive circuit of K+ ion sensor 168 is supplied via reference electrode #2 152.

Electrode 150 is a ring electrode which is located within the superior vena cava and is the anode of the electrode pair including electrode 170 supplying the stimulation pulse. It has been argued in the literature that cardioversion stimulation pulses may be more effective when the discharge is between the superior vena cava and the apex of the right ventricle. Stimulation therefore occurs using lead system 100 by a discharge between protective dome 170 which serves as the negative electrode being located at, or near the right ventricular apex and electrode 150 which serves as the positive electrode being located within the superior vena cava.

The main body of lead system 100 is covered by body compatible insulating sheath 148 of polyurethane. At the proximal end of lead system 100, bifurcation 110 produces separate insulated conductor lines 106 and 108. The main body of lead system 100 contains eleven separate mutually insulated conductors. One is required for protective dome 170, which is the stimulating electrode. Two conductors are required for K+ sensor 168 and one conductor each is required for the six sensing electrodes (164, 160, 162, 156, 158 and 154), reference electrode #2 152, and electrode 150, which serves as the anode for the stimulating pulse. The preferred means of accommodating all eleven conductors is to use a coaxial system of six multipolar conductors within the outer helix and five mutually insulated conductors in multipolar configuration within an inner helix. A similar configuration is shown in the commonly assigned U.S. patent application Ser. No. 230,572 referenced above.

The five inner leads proceed along branch 108 whereas the six outer leads proceed along branch 106. The six outer conductors terminate at connector 102 which has six separate conducting surfaces, 112, 114, 116, 118, 120 and 119 as shown. These separate conducting surfaces are mutually insulated by insulators 122, 124, 126, 128 and 129 as shown. The main connector pin housing of connector 102 is, of course, also an insulator. Similarly, the five conductors of the inner helix proceed via bifurcation 108 to connector pin 104. At that point they are connected to separate conducting surfaces 130, 132, 134, 136 and 138 which are insulated from one another by insulators 140, 142, 144 and 146 as shown. Table A shows the various conductors as related to the conducting surfaces at which they terminate.

FIG. 2c is a plan view of implantable pulse generator 26. It is comprised of an outer metallic surface 178 and an insulated surface 180 containing female connectors 182 and 184. Male connector 102 is inserted into female connector 182. Similarly, male connector 104 is inserted into female connector 184. Metallic surface 178 also serves as reference electrode #1 234 whose electrical function is discussed in detail below (i.e., metallic surface 178 refers to the physical entity and reference electrode #1 234 is the designation of its electrical function). Implantable pulse generator 26 contains the implantable electronic circuitry along with the implantable power source in the normal manner. Implantable pulse generator 26 is implanted into a surgical pocket in the manner customary for artificial cardiac pacers.

TABLE A

| Distal End | Connector Number | Conducting Surface | Function |
|---|---|---|---|
| Dome 170 | 102 | 112 | Stimulation Cathode |
| K+ Sensor 326 | 102 | 114 | Drain |
| K+ Sensor 328 | 102 | 116 | Source |
| Sense Electrode 164 | 102 | 118 | Line 60a |
| Sense Electrode 160 | 102 | 120 | Line 60c |
| Sense Electrode 162 | 102 | 119 | Line 60d |
| Sense Electrode 156 | 104 | 130 | Line 60e |
| Sense Electrode 158 | 104 | 132 | Line 60f |
| Sense Electrode 154 | 104 | 134 | Line 60b |
| Reference Electrode #2 152 | 104 | 136 | K+ Sensor Gate |
| Electrode 150 | 104 | 138 | Stimulation Anode |

FIG. 3a is intended to show schematically the manner in which the electrode pair 156 and 158 sense the direction of the current vector. As described above in reference to FIG. 2a, three mutually orthogonal electrode pairs are used for sensrng. To simplifiy the description of how each electrode pair senses mutually orthogonal electrical components of the same electrical signal, only the electrode pair 156 and 158 is shown in FIG. 3a. However, it can be readily seen that the other two electrode pairs will measure the same intracardiac ECG signal in similar fashion but along a different mutually orthogonal axis. For ease of analysis, electrode system 100 is shown in relation to arbitrary three dimensional axis system 200. This three dimensional axis system is composed of X axis 180, Y axis 182, and Z axis 178. Notice that, as in the patient's heart, ECG signal wavefront 184 from points V0 to V1 moves within three dimensional space as shown. As can be readily imagined, electrode 156 will sense the arrival of ECG signal wavefront 184 some finite amount of time before electrode 158 will sense the same wavefront. In practice, propagation within the normal myocardial tissue has been measured to be approximately 0.3 meters per second. This propagation speed corresponds to approximately 0.3 mm per millisecond. This means, of course, that there is a 3⅓ millisecond time difference between the arrival of wavefront 184 at electrode 156 and its arrival at electrode 158 for every 1 mm which separates the electrode pair for wavefront 184 traveling along the axis between electrode 156 and electrode 158. It can thus be seen that this is a convenient time interval for measuring the direction of the wavefront. If, for example, wavefront 184 were proceeding in a direction perpendicular to the axis between electrodes 156 and 158, the time of arrival would be exactly the same. Therefore, for a nine French diameter lead, the time interval between the arrival of wavefront 184 at electrode 156 and electrode 158 will vary somewhere between 0 and about 3 milliseconds.

FIG. 3b shows the wavefront 184 as viewed at implantable pulse generator 26. Signal 156a corresponds to the signal as sensed between electrode 156 and reference electrode #1 234 (the metallic case of implantable pulse generator 26). Of course, signal 156a has been shaped to produce the squarewave effect having leading edge 186, trailing edge 188 and interconnecting level 190.

Similarly, signal 158a is representative of the signal sensed between electrode 158 and reference electrode #1 234. The difference in time $\Delta t$ between leading edge 186 and leading edge 192, that is, the $\Delta t$ time from $t_0$ to $t_1$, is measure. The $\Delta t$ may also be computed from the trailing edge 188 of signal 156a to the trailing of signal 158a. This time interval is time $t_2$ to time $t_3$ and this should be the same as $\Delta t$. In either case, the $\Delta t$ time is merely representative of the travel of wavefront 187 along the axis of electrodes 156 and 158. Changes in myocardial conductivity, the effect of the conductivity of blood and of fluids, and ionic concentrations will change the absolute value of $\Delta t$. However, since the measurement of the exact angle of transfer is not required for other than diagnostic purposes, the relative measurement $\Delta t$ is sufficient for the purposes of the present invention.

U.S. Pat. No. 4,216,780 issued to Rubel et al. discusses the measurement of heart vectors using the vectorcardiographic ECG signal. However, in the example taught therein, the processing requirements are much more substantial because an exact angle is required. It must be borne in mind that, in the present invention, the relative measurement achieved with the preferred mode is sufficient.

Measurements using the other two electrode pairs (i.e., electrodes 160 and 162 and electrodes 164 and 154) are made in the same manner as is shown in FIGS. 3a and 3b. A glance at lead system 100 as shown in FIG. 2a will show that a much larger Δt is produced for the electrode pair consisting of electrodes 164 and 154 because of the larger distances involved. This disparity has not proven to be of any difficulty because only relative angles are measured, but of course, it would be relatively easy to use electrode configurations wherein the distance between electrodes 164 and 154 is comparable to the distances for the other two electrode pairs. This would simplify the mathematics but would make lead system 100 slightly more difficult to manufacture.

FIG. 3c shows the computation of an angle θ in three dimensional space showing the change of a current vector. Three dimensional axis system 198 which consists of X axis 202, Y axis 204, and Z axis 206, is used to compute angle θ. The origin is at point 208. Point 210 is arranged at coordinates X1, Y1 and Z1. This point is established wherein X1 is the Δt from a first electrode pair, Y1 is the Δt measured for a second electrode pair, and Z1 is the Δt measured for the third electrode pair. Which electrode pair corresponds to which of the coordinates is not important. What is important is that the Δt's measured all be for the same wavefront. This is not difficult since the time between successive R waves, for example, is quite substantial in relationship to the Δt's to be measured between electrode pairs.

A second point 212 is plotted in three dimensional space, using coordinates X2, Y2 and Z2. These coordinates correspond to Δt's measured from the same electrode pairs, but a different wavefront. It has been shown experimentally that, in the normal heart, the measurements from one R wave to the next will produce similar Δt's in the direction of each of the three electrode pairs since the direction of the current vector will be nearly the same. However, it has been shown experimentally by Michelson, et al, in their paper entitled "Electrophysiologic and Anatomic Correlates of Sustained Ventricular Tachyarrhythmias in a Model of Chronic Myocardial Infarction," published in *The American Journal of Cardiology*, Vol. 45 at p. 583, March, 1980, that in animal studies, the current vectors measured can be substantially different preceding the onset of ventricular fibrillation. A similar result was reached by Bruyneel in his studies on baboons as published in his article entitled "Use of Moving Epicardial Electrodes in Defining ST Segment Changes After Acute Coronary Occlusions in the Baboon in Relation to Primary Ventricular Fibrillation," published in the *The American Heart Journal*, vol. 89, No. 6, pp. 731–741, June, 1975.

As can be seen in FIG. 3c, a line 218 can be drawn between origin 208 and point 210. Similarly, a line at 214 is drawn between origin 208 and point 212. Of interest then is the angle θ between line 218 and line 214. This angle θ is representative of the change of direction of the current vector from one wavefront to another. If a standard wavefront is available (i.e., line 218 is given), θ the represents the deviation of a measured current vector from the standard. The angle θ is a relative measurement and is not intended to be the type of absolute measurement normally required in diagnostic work.

Figure 4A:
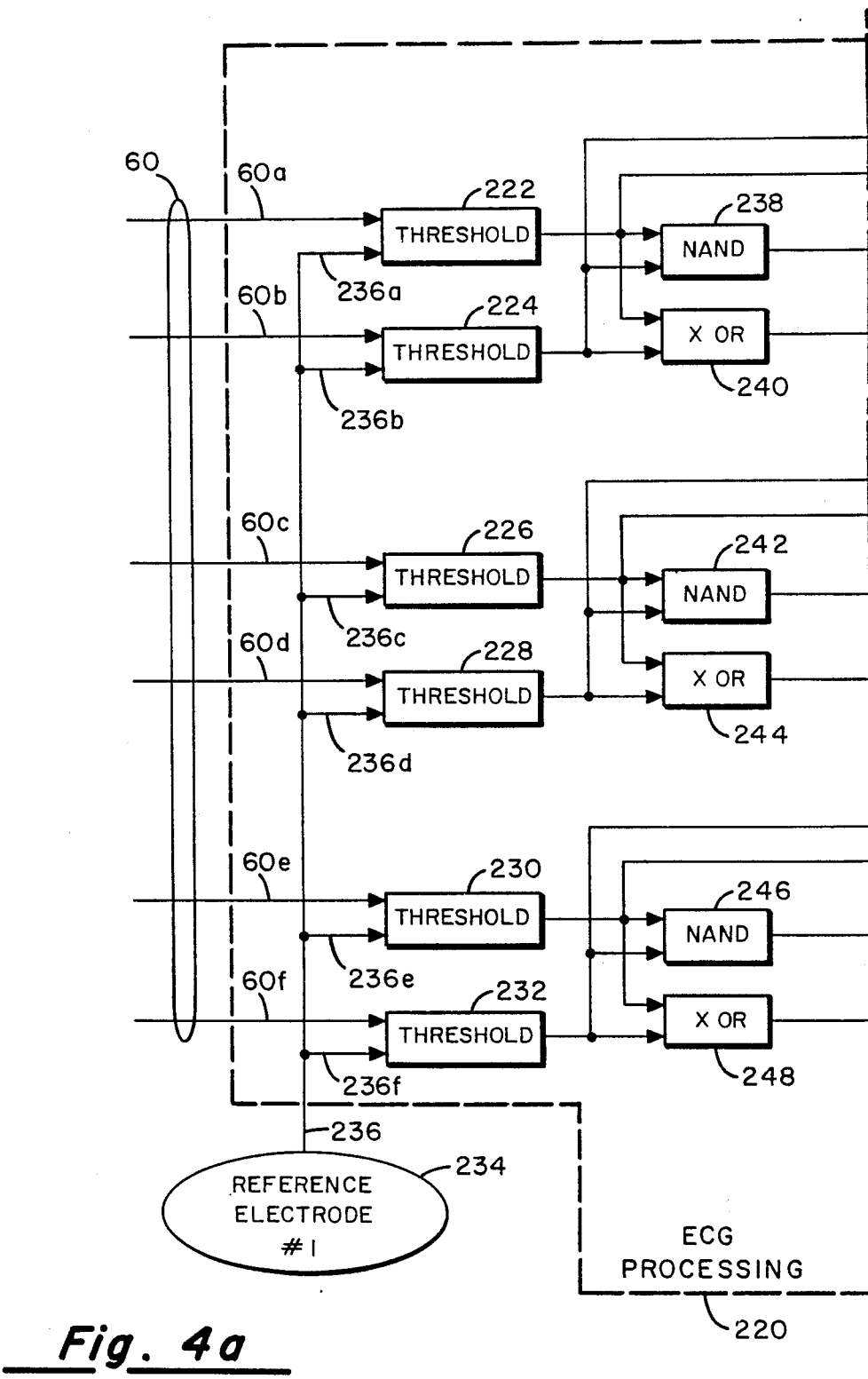
FIG. 4 is a logic diagram of element ECG processing 220 which digitally resolves the sensed current vector in three dimensional space.
Figure 4B:
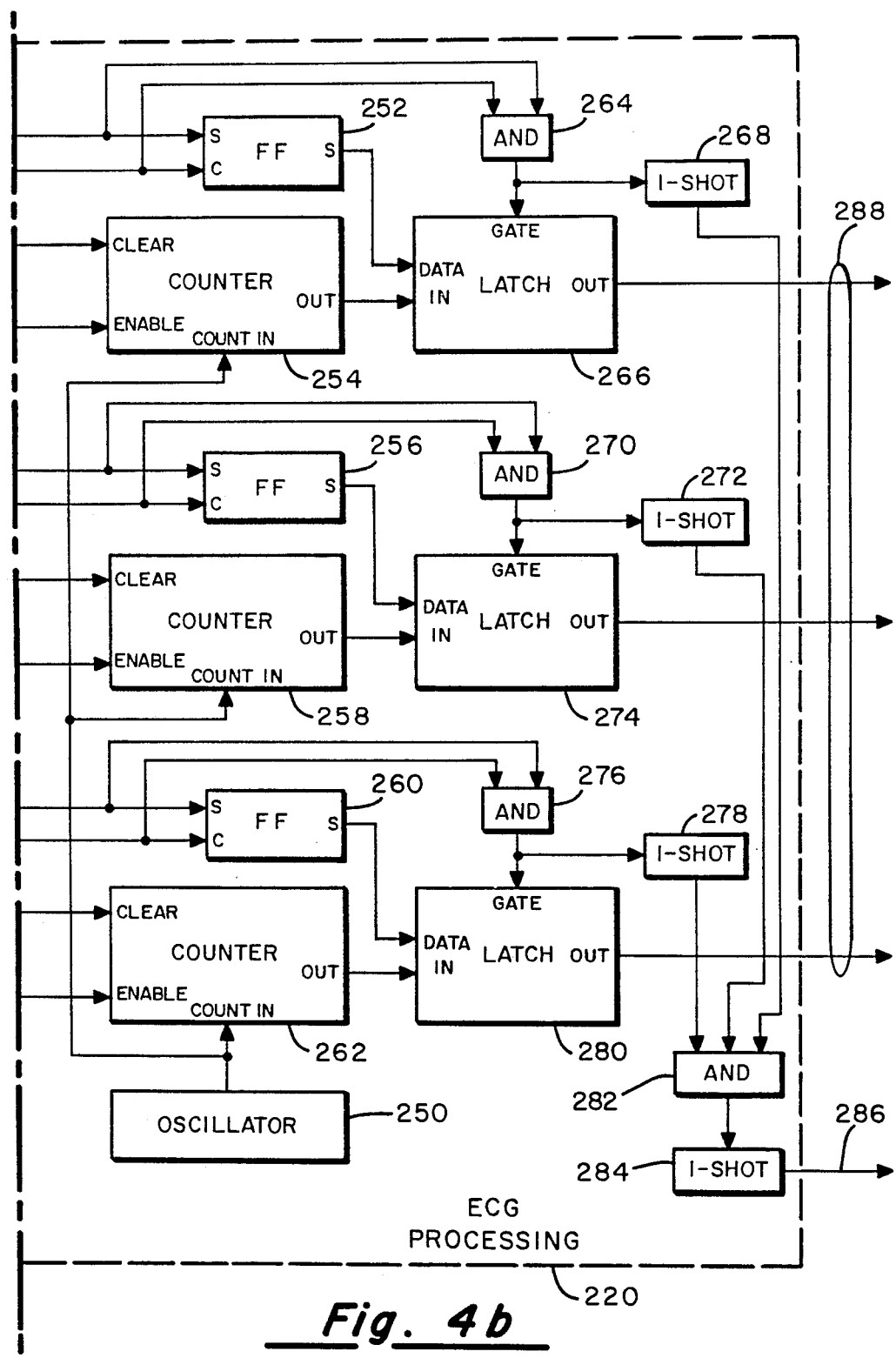

FIG. 4 is a schematic diagram of the logic required to resolve the angular relationships shown. Lines 60A, 60B, 60C, 60D, 60E and 60F correspond to the conductors from the various sensing electrodes (see also Table A). Threshold devices 222, 224, 226, 228, 230 and 232 are differential amplifiers which compare the sensed potential to reference electrode #1 234 and shape the resultant to produce squarewaves suitable for further use (see also FIG. 3b).

The signals from threshold devices 222, 224, 226, 228, 230 and 232 thus look like the signals as present in FIG. 3b. The remaining circuitry shown in FIG. 4 is used to measure the time relationship (i.e., Δt) between electrode pairs. In reference to an exemplary single electrode pair the signal corresponding to sensing electrode 164 is processed by threshold device 222 and the signal received from electrode 154 is processed by threshold device 224. NAND gate 238 supplies a clear signal to counter 254 whenever the output of threshold device 222 and threshold device 224 are both low. This corresponds to the condition when both electrodes have not yet detected the wavefront. When either electrode 164 or electrode 154 detects the onset of the wavefront, threshold device 222 or threshold device 224 supplies a signal to XOR gate 240 which enables counter 254. Having been enabled, counter 254 begins counting pulses produced by oscillator 250. A convenient rate for this counting is to have oscillator 250 supply a 1 megahertz pulse train. That means that counter 254 counts in microseconds the period between the detection of the wavefront by one of the two electrodes and stops counting after the detection of the wavefront by the second electrode. This occurs because XOR gate 240 no longer enables counter 254 when the outputs of threshold device 222 and threshold device 224 are both high.

Therefore, counter 254 has in it the number of microseconds corresponding to Δt for the electrode pair 164 and 154. Δt is supplied at the output of counter 254 to latch 266. The data is transferred into latch 266 as a result of a high signal on the gate input produced by AND gate 264. Notice that this occurs whenever threshold device 222 and threshold device 224 both produce highs. Referring back to FIG. 3b, one can see that XOR gate 240 enables counter 254 at time T0 and disables counter 254 at time T1. During the time period T1 to T2 AND gate 264 supplies the gate input to latch 266 which transfers the value of Δt from counter 254 to latch 266. Referring back to FIG. 4, one can see that a counter 254 requires twelve bit positions to store the maximum value of Δt in microseconds if Δt has a maximum value of 3 milliseconds assuming an interlectrode spacing of 1 mm. Referring again to FIG. 2a, one can see that the interelectrode spacing of electrode pair 164 and 154 is greater than for the other two electrode pairs. Therefore, for a given configuration, an additional one or two bits positions may be required for counter 254 than is required for counters 258 and 262.

Referring again to FIG. 4, it can be seen that flip-flop 252 reports the direction of the wavefront as it impinges upon the electrode pair 164 and 154. This is necessary because a directional ambiguity will occur depending upon whether or not electrode 164 senses the onset of the wavefront before electrode 154. Flip-flop 252 is set if electrode 164 senses the waveform first and is subsequently cleared by threshold 224 as electrode 154 senses the onset of the wavefront. The output of flip-flop 252 is directed to the most significant bit position of latch 266. Because this bit is gated into latch 266 at the same time as the output of counter 254, this bit position will be a 0 for the case when electrode 164 senses the wavefront first and will be a 1 for those cases in which electrode 154 first senses the wavefront.

Latch 266 supplies its output via cable 288 for subsequent processing by the microprocessor. It is possible to locate parts which have the function of counter 254 and the function latch 266 within the same monolithic device. It is, however, easier to see conceptually when one views these as separate elements. The latching of the output of counter 254 by latch 266 enables the microprocessor to have most of the cycle to view the value of $\Delta t$. Latch 266 will contain the previous value until such time as a new value is added. It will never contain a partial value of $\Delta t$ during the counting process itself.

At such time as AND gate 264 supplies the gate signal to latch 266, it also starts one-shot 268 having an output on the order of 10 milliseconds. This 10 millisecond pulse is supplied to AND gate 282 along with the output of one-shot 272 and one-shot 278. The output of AND gate 282 is supplied to one-shot 284. The output of one-shot 284 signifies that the wavefront has been detected by all six of the sensing electrodes. Because the signal is measured between each of the six electrodes and reference electrode #1 234, rather than from one electrode to the other of an electrode pair, one would expect that the signal will be viewed by each electrode for every cycle of the intracardiac ECG even if $\Delta t$ is zero (i.e., wavefront is perpendicular to the axis) for a given electrode pair. A 10 millisecond one-shot value is chosen for one-shot 268, one-shot 272, and one-shot 278 to ensure that these output signals are overlapping. One-shot 284 then supplies a signal of sufficient duration to gate the outputs of latch 266, latch 274 and latch 280 to the microprocessor. This output is on line 286, which notifies the microprocessor that new values of $\Delta t$ are available.

The processing of the other two electrode pairs is identical to the processing of electrode pairs 164 and 154. The output on cable 288 is the digital value of $\Delta t$ for each of the three electrode pairs in microseconds. Referring back to FIG. 3c, it can be seen that each of these values is plotted in three dimensional space using the arbitrary axis 198. This is accomplished using the firmware which is described in more detail below.

Figure 5:
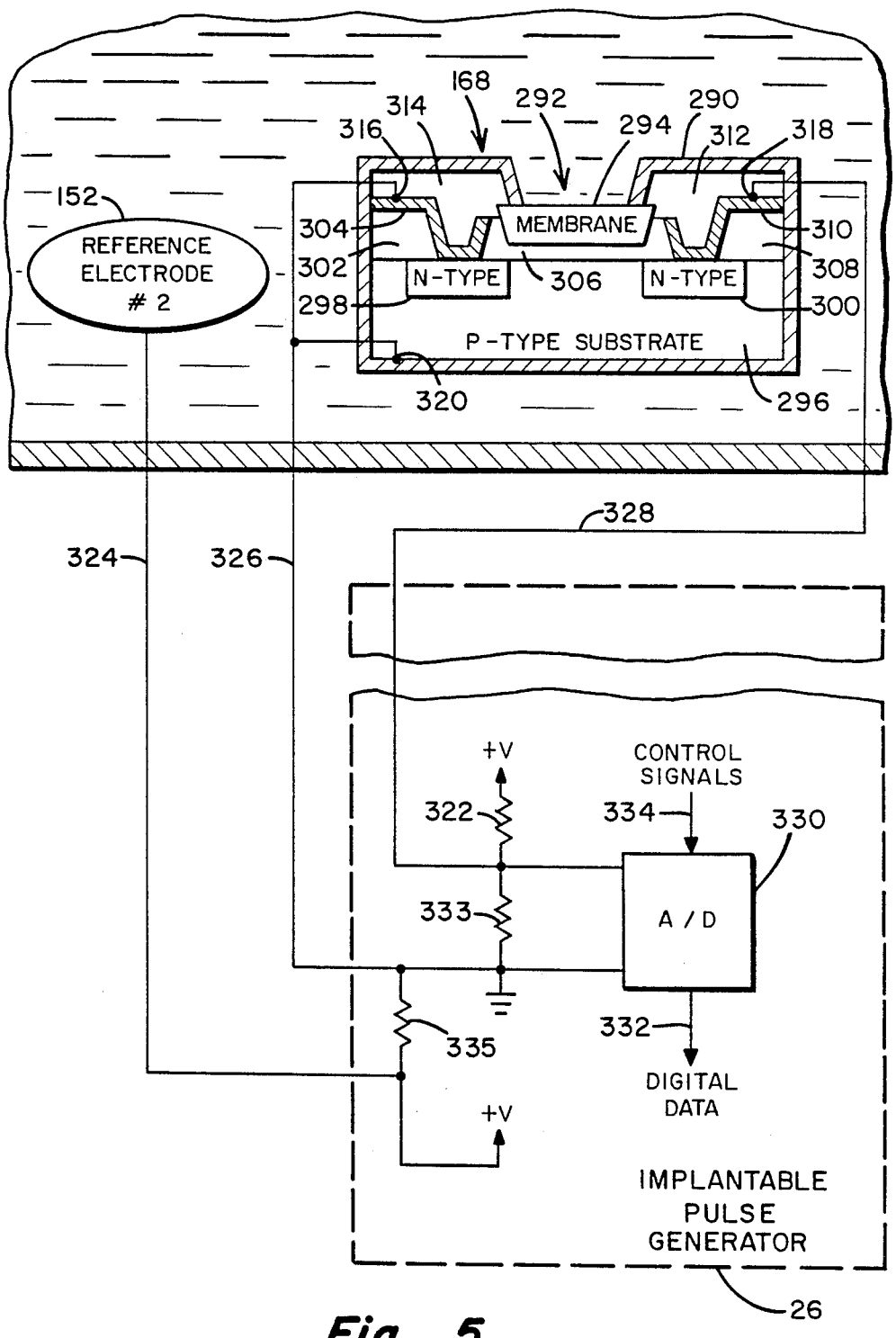
FIG. 5 is a schematic representation of the structure and circuitry of the implantable sensor used to determine the level of extracellular ionic potassium within the blood.

FIG. 5 is a schematic representation of the extracellular ionic potassium (K+) sensor. Referring back to FIG. 2a, one can see that the sensor itself is located under protective dome 170 in the position shown by the dashed lines as sensor element 168. The location of the reference electrode #2 152 is also shown. Referring again to FIG. 5 sensor element 168 and reference electrode #2 152 are located within the right ventricle of the heart after implant and are, therefore, exposed to intracardiac blood flow. For the sake of simplicity, the construction of sensing element 168 and reference electrode #2 152 are described herein briefly. For those readers interested in a more detailed description of the construction and theory of operation of an ion-sensitive field effect transistor used as sensor element 168, reference should be made to the article "Ion Sensitive Field Effect Transistors," by Janata et al., published in *Ion-Selective Electrode Review*, Vol. 1, pp. 31-79, Paragamon Press Ltd., 1979.

As stated above, K+ sensor 168 is an ion-sensitive field effect transistor. It is formed on P-type substrate 296 with N-type doping at locations 298 and 300. The source is located at 310 and the drain is located at 304. The gate is covered by an ionic potassium permeable membrane 294. The entire structure, except for membrane 294, is encapsulated by body compatible encapsulate 290. The only blood, therefore, that may impinge upon K+ sensing element 168 is via input port 292. The current flow from reference element #2 152 via inlet 292 through membrane 294 to the gate creates an electrostatic field which controls current flow from source 310 to drain 304 in the manner customary in field effect transistors. Reference electrode #2 152 must, of course, also be located within the right ventricle and be submerged in the intracardiac blood. The functional arrangement is seen in FIG. 1 and the physical arrangement of the lead body is seen in FIG. 2a.

Referring again to FIG. 5, it can be seen that the electrical circuitry associated with supplying the current for source 310 and reference electrode #2 152 is supplied by implantable pulse generator 26 via lines 328 and 324 respectively. Line 326 conducts the current from drain 304 back to implantable pulse generator 26. Conductors 324, 326 and 328 are, of course, located within lead system 100. Table A indicates which of the conductors are used. Resistor 335, between +V and ground, establishes a positive bias on reference electrode #2 152 and hence, on the gate of the ion-sensitive field effect transistor. Resistors 322 and 333 similarly establish the proper positive bias on source 310. Drain 304 is connected via line 326 to signal ground within implantable pulse generator 26. An analog-to-digital converter 330 converts the voltage drop found across resistor 333 to a digital value under control of the microprocessor 336 via line 334. The digital data is supplied to the microprocessor 336 via line 332. A low power monolithic analog-to-digital converter supplying an eight-bit conversion at moderate speed is sufficient to perform the task of A/D converter 330.

Figure 6:
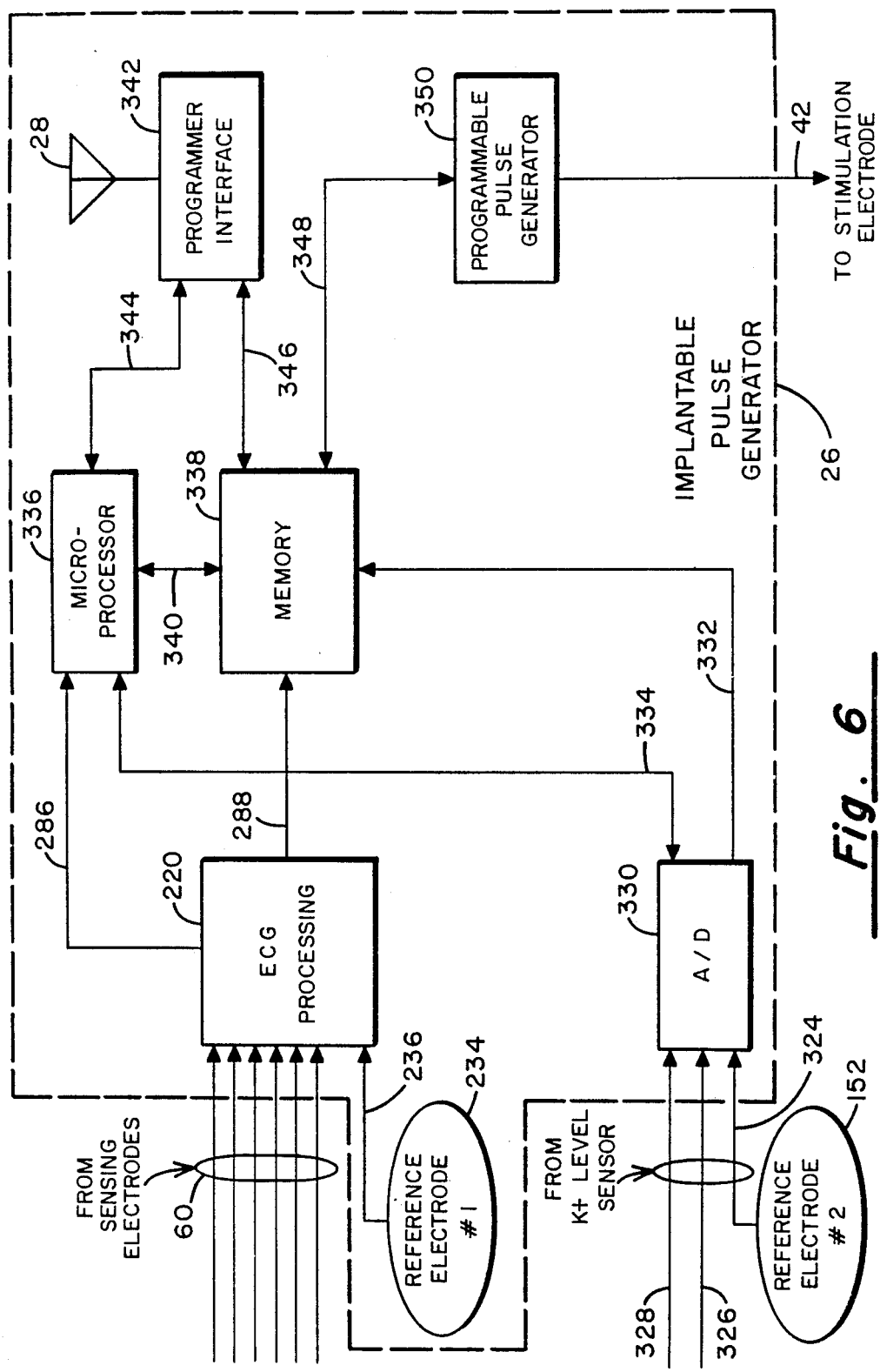
FIG. 6 is an overall block diagram of implantable pulse generator 26.

FIG. 6 is an overall block diagram of implantable pulse generator 26. ECG processing block 220 corresponds to the circuitry which may be found in FIG. 4. As explained above, ECG processing block 220 supplies the three values of $\Delta t$ to memory 338 via cable 288 as shown. The control signal indicating that the data is available is transferred via line 286 to microprocessor 336. Similarly, A/D converter 330 supplies the eight-bit digital value to memory 338 via cable 332. The CONVERT signal is supplied by microprocessor 336 to A/D converter 330 via line 334, which also supplies an acknowledgement that the data is ready. Memory 338 contains read only memory which stores the firmware instructions for the programs which are discussed below. Memory 338 also contains random access memory to be used for variable storage and the storage of input data.

Microprocessor 336 is preferably a medium performance CMOS eight-bit microprocessor such as an RCA Model 1802. It interfaces with memory 338 via access bus 340. Those of ordinary skill in the art will be readily able to interface microprocessor 336 to memory 338 using the information supplied by the device manufacturer. Programmer interface 342 is, as stated above, a device which is in common use in the art. It is constructed in the manner taught in the U.S. patents referenced above. Programmer interface 342 to microprocessor 336 via bidirectional cable 344 also interfaces with memory 338 via cable 346 which allows programmer interface 342 to store parameter data and other variables. Programmable pulse generator 350 is again an element which is common in the art. It is a pulse generator which is programmable in both energy and rate and differs from the ordinary implantable pacer pulse generator in that it has a wider range of selectable energy outputs and rates. Unlike the most common state of the art programmable pulse generators, however, programmable pulse generator 350 need not have the variability for all of the common waveshape parameters. Programmable pulse generator 350 supplies a stimulation pulse via line 42, which is located within transvenous lead system 100 at the command of microprocessor 336. The stimulation pulse enters body tissue via protective dome 170 (see also FIG. 2a).

To summarize, and in reference against to FIG. 1, most of the components of the implantable pulse generator 26 are fount in the cited prior art with the exception of the pulse generator control 44 and the blocks 52 and 58 for determining the ion and electrical current parameters measured in the heart by potassium sensor 16 and the lead system 18.

Figure 7A:
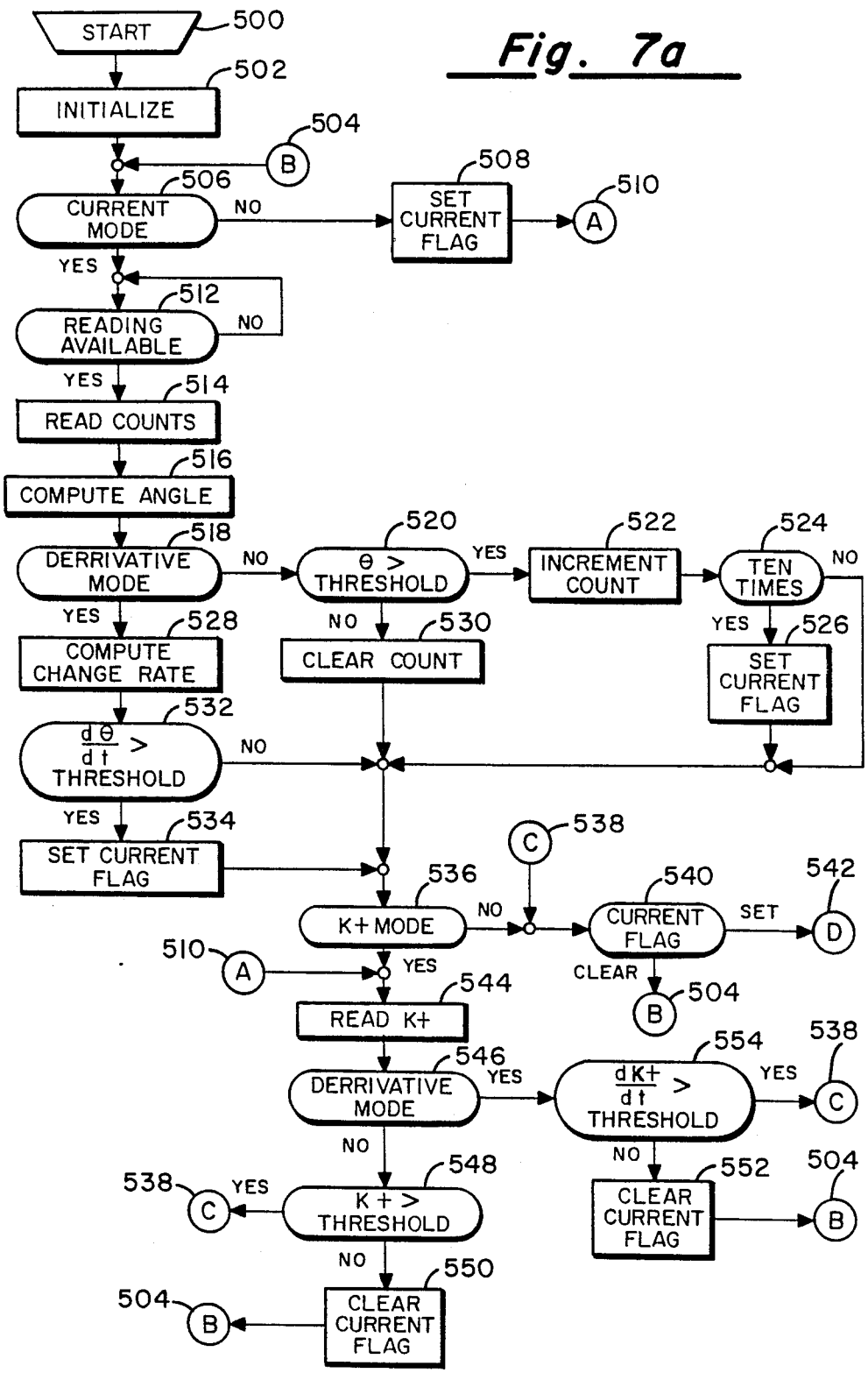
FIG. 7 is a detailed flowchart for the firmware to be executed by microprocessor 336.

Another element substantially differ from the art is depicted in FIG. 7 which is a flowchart of the main firmware program. The program is started at element 500. Various variables are initialized at element 502. Element 506 determines whether or not the current mode has been selected by the implanting physician using the programming technique. Table B shows the three sense modes that are available. Sense Mode 2 and Sense Mode 3 require the use of current measurements and will cause a branch to element 512 in FIG. 7. Sense Mode 1 will cause a branch to element 508.

If the branch is to element 508, the current flag is set and control is sent via element 510 to read the value of K+ which corresponds to Sense Mode 1.

TABLE B

| Sense Mode | Function |
| --- | --- |
| 1 | Sense K+ ONLY |
| 2 | Sense $I_y$ ONLY |
| 3 | Sense K+ and $I_y$ |

TABLE C

| Current | K+ |
| --- | --- |
| DERIVATIVE | DERIVATIVE |
| THRESHOLD | THRESHOLD |

TABLE D

| Current Derivative | Current Threshold |
| --- | --- |
| THRESHOLD $\frac{d\theta}{dt}$ | NORMAL $\theta$ THRESHOLD DEVIATION |

TABLE E

| K+ Derivative | K+ Threshold |
| --- | --- |
| THRESHOLD $\frac{dk+}{dt}$ | NORMAL K+ THRESHOLD DEVIATION |

Element 512 determines whether or not a current reading is available. Referring again to FIG. 4, it can be seen that this determination is made by interrogating line 286. In FIG. 6, one can see that line 286 is connected directly to the microprocessor 336. The interrogation of this signal can be readily accomplished using one of the serial input data bits. Referring again to FIG. 7, as soon as the reading becomes available, element 514 reads the three values of $\Delta t$. Element 516 computes the angular difference in three dimensional space of the current reading and a previous reading. The previous reading is arrived at via a programmable value unless the derivative mode has been selected as explained below. In the case of the derivative mode, the previous value becomes simply the previous reading.

Computation of the angle $\theta$ done by element 516 can be visualized in FIG. 3c. This angular computation is readily accomplished using standard coordinate transformation techniques. Again the assumption is that the angle $\theta$ is the angular distance between lines 218 and 214 wherein line 214 is a line passing through origin 208 and point 210, which is the plot of the $\Delta t$'s for each of the three electrode pairs for a previous reading (i.e., previous reading for derivative mode and programmed value in normal mode). Line 214 is defined as a line passing through origin 208 and point 212. As explained above, point 212 represents the plotted value of the three $\Delta t$'s for the present reading.

Referring again to FIG. 7, it can be seen that after computation of the angle at element 516 a determination is made whether or not the derivative mode has been selected at element 518. As can be seen in Table C, the attending physician has the option of selecting either derivative or threshold mode for current and, independently, derivative or threshold mode for K+. If the derivative mode has been selected for the current measurement, element 528 computes the time rate of change of the angle. This is readily accomplished by simply dividing the angle $\theta$ by the time period between successive readings. This corresponds to the reciprocal of the rate. Element 532 decides whether or not the time rate of change of the current vector angle is greater than the preprogrammed threshold. If it is not, control is sent to element 536. If the time rate of change is greater than the preprogrammed threshold, control is given to element 534 which sets the current flag indicating that the threshold has been exceeded. If the derivative mode has not been selected for the current sensing, element 520 determines whether or not the measured $\theta$ is different from some programmable threshold deviation by greater than a programmable amount. Table D shows the values which must be programmed for both current derivative and current threshold modes.

Referring again to FIG. 7, if element 520 finds that the measured $\theta$ does not differ by more than the threshold from the standard value, element 530 clears a temporary counter and control is sent to element 536. Should element 520 find that the threshold has been exceeded, element 522 increments a temporary counter. Element 524 determines whether or not the measured $\theta$ has differed from the standard more than a threshold amount for 10 successive times. This is necessary to prevent noise conditions or isolated anomolies from triggering the pulse generator. After ten consecutive times, element 524 transfers control to element 526 which sets the current flag indicating that the current deviation conditions have been met.

After the current measurement, if any, has been made, element 536 determines whether or not the K+ mode has been selected. Referring back to Table B, it can be seen that this corresponds to Sense Modes 1 or 3. If K+ mode has not been selected, it means that the operator has selected Sense Mode 2 and wishes to trigger the pulse generator on current vector only. Element 540 determines whether the current flag is set. If is it not set, control is returned to element 504 to read the current vector again. If the current flag is set as determined by element 540, control is transferred to element 542 to begin the generation of stimulation pulses.

Assuming that element 536 determines that K+ mode has been selected, control is sent to element 544 to read the value of K+. As was described in the above hardware description, this corresponds to reading the eight-bit value of A/D 330. Referring again to FIG. 6, it can be seen that this is accomplished by sending a CONVERT signal to A/D 330 through control line 334. The eight bit data quantity is placed into memory 338 via line 332.

As is seen in Table C, the operator may select derivative or threshold for the K+ sensing. Referring again to FIG. 7, this selection is sensed at element 546. If the threshold mode has been selected, element 548 determines whether the ionic potassium level is more than some threshold deviation from a normal value of K+. As is seen in Table E, these selections are the parameter entries which must be made in the K+ threshold mode.

If the threshold has not been exceeded, control is sent to element 550 which clears the current flag and the program returns to element 504 which reads the current vector again. If the K+ value has experienced a greater than threshold deviation, control is sent to element 538 which interrogates the current flag at element 540. If the current flag is also set, it means that stimulation is required and control is sent to element 542. If the current flag is not set, control returns to element 504 to continue sensing.

If element 546 determines that the derivative mode has been selected, element 554 determines whether the time rate of change of ionic potassium level exceeds some programmed threshold. Again, Table E shows that parameter selection. If element 554 determines that the threshold value has been exceeded, control is sent via element 538 to element 540 to determine if the current flag is set. On the other hand, if the threshold value has not been exceeded as determined by element 554, element 552 clears the current flag and control is sent via element 504 to continue current sensing.

Control arrives at element 556 as a result of the determination that stimulation pulses are required. Table F shows the three output modes. Output Mode 1 provides a fixed rate programmable from 100 to 400 bpm with a fixed energy output programmable from $10^{-5}$ to 1 joule. Output Mode 2 provides for a fixed rate programmable from 60 to 120 bpm with a fixed energy output programmable from $10^{-5}$ to $10^0$ joules. Output Mode 3 provides for a fixed rate programmable from 60 to 120 bpm and an energy output which begins at $10^{-5}$ joules and increases to 1 joule by 1 order of magnitude each 10 seconds.

Element 556 clears the temporary amplitude value which is required for Output Mode 3 only. This is a way of initializing Output Mode 3. Element 560 determines whether it is time to generate the next stimulation pulse and retains control until that time. This is accomplished using the programmed value which is somewhere between 60 and 400 bpm. Element 562 actually generates the stimulation pulse at the proper energy level. Element 564 determines whether this is a fixed energy mode and if the determination is no, element 566 increments the temporary amplitude at the proper time. This completes the generation of the first stimulation pulse. At this point, the determination must be made at which point to generate additional stimulation pulses or to terminate stimulation. Table G shows the five termination modes. In Termination Mode 1, the stimulation may be terminated only by the current vector or a derivative of the current vector being returned to within some programmable threshold value.

TABLE F

| Output Mode | Rate | Energy |
|---|---|---|
| 1 | FIXED (100–400 BPM) | FIXED ($10^{-5}$ to $10^0$ joules) |
| 2 | FIXED (60–120 BPM) | FIXED ($10^{-5}$ to $10^0$ joules) |
| 3 | FIXED (60–120 BPM) | INCREASING BY 10× |

TABLE G

| Termination Mode | Function | Program Values |
|---|---|---|
| 1 | $I_v$ ONLY | THRESHOLD |
| 2 | K+ ONLY | THRESHOLD |
| 3 | K+ AND $I_v$ | K+ THRESHOLD AND $I_v$ THRESHOLD |
| 4 | K+ OR $I_v$ | K+ THRESHOLD AND $I_v$ THRESHOLD |
| 5 | TIME | DURATION |

In Termination Mode 2 stimulation will continue until the K+ level or time rate of change of K+ level returns to some threshold value. Termination Mode 3 requires both the K+ and current vector values and/or derivatives thereof to return within threshold values. Termination Mode 4 will cease stimulation pulses whenever the ionic potassium level or the current vector values or derivatives thereof return to within some threshold values. Notice that, in all cases, the thresholds that are programmed may be different from those for beginning stimulation. Termination Mode 5 allows for termination after the expiration of some programmable period of time.

Referring again to FIG. 7, element 568 determines whether or not Termination Mode 5 (i.e., duration mode) has been selected. If this is answered in the affirmative, element 570 determines whether it has reached the time to terminate. If the answer is no, control is returned to element 558 which awaits the generation of the next stimulation pulse. If element 570 has determined that it is time to terminate stimulation, element 572 clears the current flag and control is returned to element 504 to continue sensing.

Assuming that Termination Mode 5 has not been selected, element 574 determines whether or not there is to be termination on current value. This corresponds to Termination Modes 1, 3 and 4. If the current value is irrelevant (i.e., Termination Mode 2), control is sent to element 590 to read the value of K+. Assuming, however, that termination may be achieved by current value, element 576 awaits the availability of the current value reading. The reading is accomplished at element 578, which is similar to operation at element 514. Angle $\theta$ is again computed at element 580 and element 582 determines whether or not the derivative mode has been selected for termination. Notice that this is independent from the selection of the BEGIN STIMULATION Mode such that, beginning stimulation may be a function of the derivative of the angle $\theta$ and ending termination may be a function of just angle $\theta$ or vice versa. If the derivative mode has been selected, the time rate of change of angle $\theta$ is again computed at element 600 and the determination is made of whether or not the time rate of change of angle $\theta$ is less than the termination threshold. If it is not, control is returned to element 558 for the generation of the stimulation pulse. If it is however within the threshold, control is transferred to element 586.

If element 582 determines that the derivative mode has not been selected for termination, element 584 determines whether or not the measured θ is less than the deviation allowed by the preprogrammed threshold. If not, control is again sent to element 558 for the generation of the next stimulation pulse. If the angle θ is now within the stimulation threshold, then element 586 determines whether or not there is a termination on the value of K+. If it is not, as is the case for Termination Modes 1 and 4, element 588 clears the current flag and control is sent via element 504 to begin sensing prior to the reiniation of stimulation. If element 586 determines that the current value of K+ must be measured to determine whether or not termination is to take place, element 590 reads K+ as discussed above. Element 592 determines whether the derivative mode has been selected. If the derivative mode has not been selected, element 596 determines whether or not the K+ value read is within the termination threshold. If it is not, control is sent via element 558 to generate the next stimulation pulse. If the value of K+ is now within the termination threshold, element 596 transfers control to element 598 to clear the current flag. From that point, control is sent to element 504 for the purpose of continuing the sensing operation.

Should element 592 determine that the derivative mode has been selected, element 594 will determine whether or not the time rate of change of K+ is within the programmed threshold. If it is not, control is sent via element 558 to prepare the next stimulation pulse. If the time rate of change of K+ is determined to be within the termination threshold, element 598 clears the current flag and control is sent via element 504 to again sense.

The main firmware program as discussed in relationship to the flowchart on FIG. 7 is that control program which is initiated at the start of implantation and continues throughout the life of the device. It operates in the task mode in the lowest state of microprocessor 336. Notice that it has two basic functions. The first being the sensing to determine when stimulation should be initiated and the second to continue stimulation and sensing until such time as a determination is made that stimulation should cease. This firmware program is coded in the language of microprocessor 336, and located within a read only memory comprising a portion of memory 338.

FIG. 8 is flowchart of an interrupt firmware program to be a part of the ROM in memory 338. Whenever programming is initiated, the normal sensing and stimulation functions cease and microprocessor 336 executes the interrupt program. Entry is achieved via element 700 which is a result of the interrupt vectoring microprocessor 336 to programmer interrupt program 700. Element 702 establishes the synchronization required by the protocol. Element 704 updates the parameters as shown in Tables B, C, D, E, F and G. Element 706 sends the telemetry acknowledgement and element 708 reinitializes the program. This is required because the previous program had been running and had stored some temporary variables which are no longer valid after the entry of different program parameters and operating modes. At that point the interrupt routine has been completed and control is sent to element 504 to begin the sensing operation.

The values chosen for the various programmable thresholds are, of course, a matter of medical decision. However, it has been found that an extracellular ionic potassium level of 4 millimoles/liter is about average for intracardiac blood in healthy adults. Deviations of more than about ±1.5 millimoles/liter have been found to be suspect. Similarly, a dk+/dt of greater than about ±1.0 millimole/liter/minute is probably indicative of the onset of fibrillation.

The current vector angles measured are relative as explained above. However, deviations of 90°/minute are probably also indicative of the onset of fibrillation.

The preferred mode of the present invention is described as having a considerable number of programmable features which allow the attending physician to select the desired therapy. These parameters may be selected with the aid of the substantial information available in the literature concerning the relationship of extracellular ionic potassium imbalance and its relationship to ventricular tachyarrhythmias and ventricular fibrillation and the effects of depolarization current direction changes. Those of ordinary skill in the art will be readily able to apply the teaching found herein to the prevention of ventricular fibrillation through the sensing of other parameters such as extracellular ionic sodium.

We claim:

1. A system for sensing the direction of propagation of depolarization waves within the heart, comprising:
    an elongated insulative lead body having a proximal end and a distal end;
    first electrode mounted to said lead body;
    second electrode mounted to said lead body, displaced 180 degrees circumferentially from said first electrode;
    third electrode mounted to said lead body, displaced from said first and second electrodes;
    fourth electrode mounted to said lead body, displaced axially from said third electrode, wherein said first, second, third and fourth electrodes are mounted to section of said lead body of length insertable within a single chamber of a human heart;
    indifferent electrode means for electrically contacting the body and providing an electrically common reference point outside said chamber of said heart;
    first sensing means electrically coupled to said first electrode and to said indifferent electrode means for sensing the arrival of a depolarization wave at said first electrode and for generating a first sensing signal in response thereto;
    second sensing means electrically coupled to said second electrode and to said indifferent electrode means for sensing the arrival of said depolarization wave at said second electrode and for generating a second sensing signal indicative thereof;
    third sensing means electrically coupled to said third electrode and to said indifferent elctrode for sensing the arrival of said depolarization wave at said third electrode and for generating a third sensing signal indicative thereof;
    fourth sensing means electrically coupled to said fourth electrode and to said indifferent electrode means for sensing the arrival of said depolarization wave at said fourth electrode and for generating a fourth sensing means signal indicative thereof; and
    direction determining means coupled to said first, second, third, and fourth sensing means for determining the direction of propagation of said depolarization wave within said chamber of said human heart in response to said first, second, third and fourth sensing signals, wherein said direction determining means comprises:
first order determining means coupled to said first and second sensing means for determining the order of occurrence of said first and second sensing signals and generating a first directional signal indicative thereof; and
second order determining means coupled to said third and fourth sensing means for determining the order of occurrence of said third and fourth sensing signals and for generating a second directional signal indicative thereof.

2. A system for sensing electrical depolarization wave signals within a single chamber of the heart, comprising:
an elongated insulative lead body having a proximal end and a distal end;
first electrode mounted to said lead body;
second electrode mounted to said lead body, displaced circumferentially 180 degrees from said first electrode;
a third electrode mounted to said lead body, displaced circumferentially 90 degrees from said first and second electrodes;
a fourth electrode mounted to said lead body, displaced circumferentially 180 degrees from said third electrode, said first, second, third and fourth electrodes mounted to said lead body, displaced along a segment of said lead body of length insertable within a single chamber of said human heart;
four mutually insulated conductors within said lead body, each coupled to a different one of said first, second, third and fourth electrodes;
indifferent electrode means for electrically contacting the body and providing an electrically common reference point outside said single chamber of said heart;
first sensing means electrically coupled to said first electrode and to said indifferent electrode for sensing the arrival of a depolarization wave at said first electrode and for generating a first sensing signal indicative thereof;
second sensing means electrically coupled to said second electrode and to said indifferent electrode for sensing the arrival of said depolarization wave at said second electrode and for generating a second sensing signal indicative thereof;
third sensing means electrically coupled to said third electrode and to said indifferent electrode for sensing the arrival of said depolarization wave at said third electrode and for generating a third sensing signal indicative thereof;
fourth sensing means electrically coupled to said fourth electrode and to said indifferent electrode means for sensing the arrival of said depolarization wave at said fourth electrode and for generating a fourth sensing signal indicative thereof; and
direction determining means coupled to said first, second, third and fourth sensing means for determining the direction of propagation of said depolarization wave within said chamber of said heart, in response to said first, second, third and fourth sensing signals, wherein said direction determining means comprises:
first order determining means coupled to said first and second sensing means for determining the order of occurrence of said first and second sensing signals and generating a first directional signal indicative thereof; and
second order determining means coupled to said third and fourth sensing means for determining the order of occurrence of said third and fourth sensing signals and for generating a second directional signal indicative thereof.

3. A system for sensing electrical depolarization wave signals within a single chamber of the heart, comprising:
an elongated insulative lead body having a proximal end and a distal end;
first electrode mounted to said lead body;
second electrode mounted to said lead body, displaced circumferentially 180 degrees from said first electrode;
a third electrode mounted to said lead body, displaced circumferentially 90 degrees from said first and second electrodes;
a fourth electrode mounted to said lead body, displaced circumferentially 180 degrees from said third electrode, said first, second, third and fourth electrodes mounted to said lead body, displaced along a segment of said lead body of length insertable within a single chamber of said human heart;
four mutually insulated conductors within said lead body, each coupled to a different one of said first, second, third and fourth electrodes;
indifferent electrode means for electrically contacting the body and providing an electrically common reference point outside said single chamber of said heart;
first sensing means electrically coupled to said first electrode and to said indifferent electrode for sensing the arrival of a depolarization wave at said first electrode and for generating a first sensing signal indicative thereof;
second sensing means electrically coupled to said second electrode and to said indifferent electrode for sensing the arrival of said depolarization wave at said second electrode and for generating a second sensing signal indicative thereof;
third sensing means electrically coupled to said third electrode and to said indifferent electrode for sensing the arrival of said depolarization wave at said third electrode and for generating a third sensing signal indicative thereof;
fourth sensing means electrically coupled to said fourth electrode and to said indifferent electrode means for sensing the arrival of said depolarization wave at said fourth electrode and for generating a fourth sensing signal indicative thereof; and
direction determining means coupled to said first, second, third and fourth sensing means for determining the direction of propagation of said depolarization wave within said chamber of said heart, in response to said first, second, third and fourth sensing signals, wherein said direction determining means comprises:
a first time interval measuring means coupled to said first and second sensing means for measuring the time interval between occurrence of said first and second sensing signals and generating a first time interval signal indicative thereof; and
second time interval determining means coupled to said third and fourth sensing means for determining the time interval between occurrence of said third and fourth sensing signals and generating a second time interval signal indicative thereof.

4. A system for sensing the direction of propagation of depolarization waves within the heart, comprising:

an elongated insulative lead body having a proximal end and a distal end;

first electrode mounted to said lead body;

second electrode mounted to said lead body, displaced 180 degrees circumferentially from said first electrode;

third electrode mounted to said lead body, displaced from said first and second electrodes;

fourth electrode mounted to said lead body, displaced axially from said third electrode, wherein said first, second, third and fourth electrodes are mounted to section of said lead body of length insertable within a single chamber of a human heart;

indifferent electrode means for electrically contacting the body and providing an electrically common reference point outside said chamber of said heart;

first sensing means electrically coupled to said first electrode and to said indifferent electrode means for sensing the arrival of a depolarization wave at said first electrode and for generating a first sensing signal in response thereof;

second sensing means electrically coupled to said second electrode and to said indifferent electrode means for sensing the arrival of said depolarization wave at said second electrode and for generating a second sensing signal indicative thereof;

third sensing means electrically coupled to said third electrode and to said indifferent electrode for sensing the arrival of said depolarization wave at said third electrode and for generating a third sensing signal indicative thereof;

fourth sensing means electrically coupled to said fourth electrode and to said indifferent electrode means for sensing the arrival of said depolarization wave at said fourth electrode and for generating a fourth sensing means signal indicative thereof; and direction determining means coupled to said first, second, third, and fourth sensing means for determining the direction of propagation of said depolarization wave within said chamber of said human heart in response to said first, second, third and fourth sensing signals, wherein said direction determining means comprises:

a first time interval measuring means coupled to said first and second sensing means for measuring the time interval between occurrence of said first and second sensing signals and generating a first time interval signal indicative thereof; and second time interval determining means coupled to said third and fourth sensing means for determining the time interval between occurrence of said third and fourth sensing signals and generating a second time interval signal indicative thereof.

5. A system according to claim 3 or 4 wherein said direction determining means further comprises:

first order determining means coupled to said first and second sensing means for determining the order of occurrence of said first and second sensing signals and for generating a first directional signal indicative thereof; and second order determining means coupled to said third and fourth sensing means for determining the order of occurrence of said third and fourth sensing signals and generating a second directional signal indicative thereof.

6. A system according to claim 5 wherein said direction determining means further comprises:

processing means coupled to said first and second time interval measuring means and to said first and second order determining means for determining the direction of depolarization wave propagation within said chamber of said heart in response to said first and second time interval signals and in response to said first and second directional signals.

7. A system for sensing electrical depolarization wave signals within a single chamber of the heart, comprising:

an elongated insulative lead body having a proximal end and a distal end;

first electrode mounted to said lead body;

second electrode mounted to said lead body, displaced circumferentially 180 degrees from said first electrode;

a third electrode mounted to said lead body, displaced circumferentially 90 degrees from said first and second electrodes;

a fourth electrode mounted to said lead body, displaced circumferentially 180 degrees from said third electrode, said first, second, third and fourth electrodes mounted to said lead body, displaced along a segment of said lead body of length insertable within a single chamber of said human heart;

four mutually insulated conductors within said lead body, each coupled to a different one of said first, second, third and fourth electrodes;

indifferent electrode means for electrically contacting the body and providing an electrically common reference point outside said single chamber of said heart;

first sensing means electrically coupled to said first electrode and to said indifferent electrode for sensing the arrival of a depolarization wave at said first electrode and for generating a first sensing signal indicative thereof;

second sensing means electrically coupled to said second electrode and to said indifferent electrode for sensing the arrival of said depolarization wave at said second electrode and for generating a second sensing signal indicative thereof;

third sensing means elctrically coupled to said third electrode and to said indifferent electrode for sensing the arrival of said depolarization wave at said third electrode and for generating a third sensing signal indicative thereof;

fourth sensing means electrically coupled to said fourth electrode and to said indifferent electrode means for sensing the arrival of said depolarization wave at said fourth electrode and for generating a fourth sensing signal indicative thereof;

direction determining means coupled to said first, second, third and fourth sensing means for determining the direction of propagation of said depolarization wave within said chamber of said heart, in response to said first, second, third and fourth sensing signals;

a fifth electrode, mounted to said lead body, displaced from said first, second, third and fourth electrode;

a sixth electrode mounted to said body, displaced axially from said fifth electrode, said fifth and sixth electrodes mounted to said segment of said elongated lead body;

two additional mutually insulated conductors within said lead body each coupled to a different one of said fifth and sixth electrodes;

fifth sensing means electrically coupled to said fifth electrode and to said indifferent electrode means for sensing the arrival of said depolarization wave at said fifth electrode and for generating a sixth sensing signal in response thereto; and sixth sensing means electrically coupled to said sixth electrode and to said indifferent electrode for sensing the arrival of said depolarization wave at said sixth electrode and for generating a sixth sensing signal in response thereto, wherein said fifth and sixth sensing means are coupled to said direction determining means and wherein said direction determining means determines the direction of propagation of said depolarization wave within said chamber of said heart in response to said first, second, third, fourth, fifth and sixth sensing signals; and wherein said direction determining means comprises:

first order determining means coupled to said first and second sensing means for determining the order of occurrence of said first and second sensing signals and for generating a first directional signal indicative thereof;

second order determining means coupled to said third and fourth sensing means for sensing the order of occurrence of said third and fourth sensing signals and for generating a second directional signal indicative thereof; and third order determining means coupled to said fifth and sixth electrodes for sensing the order of occurrence of said fifth and sixth sensing signals and for generating a third directional signal indicative thereof.

8. A system for sensing electrical depolarization wave signals within a single chamber of the heart, comprising:

an elongated insulative lead body having a proximal end and a distal end;

first electrode mounted to said lead body;

second electrode mounted to said lead body, displaced circumferentially 180 degrees from said first electrode;

a third electrode mounted to said lead body, displaced circumferentially 90 degrees from said first and second electrodes;

a fourth electrode mounted to said lead body, displaced circumferentially 180 degrees from said third electrode, said first, second, third and fourth electrodes mounted to said lead body, displaced along a segment of said lead body of length insertable within a single chamber of said human heart;

four mutually insulated conductors within said lead body, each coupled to a different one of said first, second, third and fourth electrodes;

indifferent electrode means for electrically contacting the body and providing an electrically common reference point outside said single chamber of said heart;

first sensing means electrically coupled to said first electrode and to said indifferent electrode for sensing the arrival of a depolarization wave at said first electrode and for generating a first sensing signal indicative thereof;

second sensing means electrically coupled to said second electrode and to said indifferent electrode for sensing the arrival of said depolarization wave at said second electrode and for generating a second sensing signal indicative thereof;

third sensing means electrically coupled to said third electrode and to said indifferent electrode for sensing the arrival of said depolarization wave at said third electrode and for generating a third sensing signal indicative thereof;

fourth sensing means electrically coupled to said fourth electrode and to said indifferent electrode means for sensing the arrival of said depolarization wave at said fourth electrode and for generating a fourth sensing signal indicative thereof;

direction determining means coupled to said first, second, third and fourth sensing means for determining the direction of propagation of said depolarization wave within said chamber of said heart, in response to said first, second, third and fourth sensing signals;

a fifth electrode, mounted to said lead body, displaced from said first, second, third and fourth electrode;

a sixth electrode mounted to said body, displaced axially from said fifth electrode, said fifth and sixth electrodes mounted to said segment of said elongated lead body;

two additional mutually insulated conductors within said lead body each coupled to a different one of said fifth and sixth electrodes;

fifth sensing means electrically coupled to said fifth electrode and to said indifferent electrode means for sensing the arrival of said depolarization wave at said fifth electrode and for generating a sixth sensing signal in response thereto; and sixth sensing means electrically coupled to said sixth electrode and to said indifferent electrode for sensing the arrival of said depolarization wave at said sixth electrode and for generating a sixth sensing signal in response thereto, wherein said fifth and sixth sensing means are coupled to said direction determining means and wherein said direction determining means determines the direction of propagation of said depolarization wave within said chamber of said heart in response to said first, second, third, fourth, fifth and sixth sensing signals; and wherein said direction determining means comprises:

first time interval determining means coupled to said first and second sensing means for determining the time interval between said first and second sensing signals and generating a first time interval signal indicative thereof;

second time interval determining means coupled to said third and fourth sensing means for determining the time interval between occurrences of said third and fourth sensing signals and for generating a second time interval signal indicative thereof; and third time interval determining means coupled to said fifth and sixth sensing means for determining the time interval between the occurrence of said fifth and sixth sensing signals and for generating a third time interval signal indicative thereof.

9. A system according to claim 8, wherein said order determining means further comprises:

a first order determining means coupled to said first and second sensing means for determining the order of occurrence of said first and second sensing signals and for generating a first directional signal indicative thereof;

second order determining means coupled to said third and fourth sensing means for determining the order of occurrence of said third and fourth sensing signals and for generating a second directional signal indicative thereof; and third order determining means coupled to said fifth and sixth sensing means for determining the order of occurrence of said fifth and sixth sensing signals and for generating a third directional signal indicative thereof.

10. A system according to claim 9 wherein said direction determining means further comprises:

processor means coupled to said first, second, and third time interval determining means and to said first, second and third order determining means for determining the direction of propagation of a depolarization wave within said chamber of said heart in response to said first, second and third time interval signals and in response to said first, second and third directional signals.

11. A system for determining the direction of propagation of a depolarization wave within a single chamber of a human heart, comprising:

first electrode means for location within said chamber of said human heart;

second electrode means for location within said chamber of said human heart, spaced from said first electrode means and defining a sensing axis between said first and second electrode means;

indifferent electrode means for location within the body, outside of said chamber of said heart;

first sensing means coupled to said first and third electrodes for sensing the arrival of a depolarization wave at said first electrode and for generating a first sensing signal indicative thereof;

second sensing means coupled to said second and third electrodes for sensing the arrival of said depolarization wave at said second electrode; and order determining means, coupled to said first and second sensing means for determining the order of occurrence of said first and second sensing signals and for generating a first directional signal indicative thereof.

12. A system according to claim 11 further comprising first time interval determining means coupled to said first and second sensing means for determining the time interval intermediate said first and second sensing signals and for generating a first time interval signal indicative thereof.

13. A system according to claim 11, further comprising:

third and fourth electrode means for location within said chamber of said heart, said third and fourth electrode means defining a sensing axis orthogonal to the sensing axis defined by said first and second electrodes;

third sensing means coupled to said third electrode means and said indifferent electrode means for sensing the arrival of said depolarization wave at said third electrode means and for generating a third sensing signal indicative thereof;

fourth sensing means coupled to said fourth electrode and to said indifferent electrode means for sensing the arrival of said depolarization wave at said fourth electrode means and for generating a fourth sensing signal indicative thereof;

second order determining means coupled to said third and fourth electrodes for determining the order of occurrence of said third and fourth sensing signals and for generating a second directional signal indicative thereof; and processing means coupled to said first and second order determining means for determining the direction of propagation of a depolarization wave within said chamber of said heart in response to said first and second directional signals.

14. A system according to claim 13 further comprising first time interval determining means coupled to said first and second sensing means for determining the time interval between occurrence of said first and second sensing signals and for generating a first time interval signal indicative thereof;

second time interval determining means coupled to said third and fourth sensing means for determining the time interval between occurrence of said third and fourth sensing signals and for generating a second time interval signal indicative thereof; and wherein said processing means is coupled to said first and second time interval determining means and wherein said processing means determining said direction of propagation of said depolarization wave within said chamber of said heart in response to said first and second directional signals and to said first and second time interval signals.

15. A system for determining the direction of propagation of a depolarization wave within a single chamber of a human heart, comprising:

first and second electrode means for location within said chamber of said human heart and for determining a first sensing axis;

third and fourth electrode means for location within said chamber of said human heart and for determining a second sensing axis perpendicular to said first sensing axis;

indifferent electrode means for location within the body, outside of said chamber of said human heart;

first sensing means coupled to said first electrode means and to said indifferent electrode means for sensing the arrival of a depolarization wave at said first electrode means and generating a first sensing signal indicative thereof;

second sensing means coupled to said second electrode means and to said indifferent electrode means for sensing the arrival of said depolarization wave at said second electrode means and for generating a second sensing signal indicative thereof;

third sensing means coupled to said third electrode means and to said indifferent electrode means for sensing the arrival of said depolarization wave at said third electrode means and for generating a third sensing signal indicative thereof;

fourth sensing means coupled to said fourth electrode means and to said indifferent electrode means for sensing the arrival of said depolarization wave at said fourth electrode means and for generating a fourth sensing signal indicative thereof;

first time interval sensing means coupled to said first and second means for determining the time interval intermediate said first and second sensing signals;

second time interval determining means coupled to said third and fourth sensing means for determining the time interval intermediate the occurrence of said third and fourth sensing signals; and processing means coupled to said first and second time interval determining means for determining the direction of propagation of a depolarization wave within said chamber of said human heart in response to said first and second time interval signals.

* * * * *